United States Patent [19]

Bell

[11] Patent Number: 4,729,661
[45] Date of Patent: Mar. 8, 1988

[54] ASYNCHRONOUS SERIAL CUVETTE READER

[75] Inventor: Michael Bell, Corona, Calif.

[73] Assignee: Specialty Medical Industries, Inc., Garden Grove, Calif.

[21] Appl. No.: 760,107

[22] Filed: Jul. 29, 1985

[51] Int. Cl.[4] .................................. G01N 21/00
[52] U.S. Cl. .............................. 356/437; 356/246
[58] Field of Search ............ 356/246, 436, 432, 440

[56] References Cited

U.S. PATENT DOCUMENTS 3,544,225 12/1970 Wattenburg et al. ............ 356/440
3,864,044 2/1975 Lyshkow ......................... 356/436

Primary Examiner—R. A. Rosenberger
Assistant Examiner—Crystal D. Cooper
Attorney, Agent, or Firm—Beehler, Pavitt, Siegemund, Jagger, Martella & Dawes

[57] ABSTRACT

A plurality of test cells in a cuvette is optically measured while the cuvette is manually moved through a sensing light beam. The cuvette is exposed in an open channel exposed to ambient light and is manually moved through the sensing light beam at an arbitrary rate. Abrupt changes in the optical density sensed by the beam are used to trigger the storage of the light beam intensity as an accepted measurement. The abrupt change is determined by comparing the currently read optical density of the cell against a predetermined moving average of previously read optical densities. A modulated sensing beam is received by a photodetector and converted from an analog to a digital signal by a fast A-to-D converter. The output of the A-to-D converter is coupled to a central processing unit which also includes as its input a bar code reader reading from a optically coded strip such instructions which are necessary to describe the number of cells, the test to be determined and other processing or reporting information. Abrupt changes in optical density caused by the passage of the edge of a cuvette cell triggers the generation of an accepted measurement from which an enzyme immunoassay test is performed.

1 Claim, 6 Drawing Figures

ASYNCHRONOUS SERIAL CUVETTE READER

BACKGROUND OF THE INVENTION

1. Field of the Invention

The present invention relates to an apparatus and methodology for measuring optical properties of a series of cells, and more particularly relates to an optical reader and analyzer for measuring reactions with respect to multiple samples of biological or chemical substances which have been treated with known reagents.

2. Description of the Prior Art

Automated or semiautomated apparatus for testing and processing information derived from multiple specimens subject to a reaction with a known reagent are well known in the art. Horne, "Apparatus for Monitoring Chemical Reactions," U.S. Pat. No. 4,430,229 is typical of an automated system for measuring a plurality of prepared slides which are synchronously advanced through the analysis apparatus by a rotary table. Jones, "Sample Cup Holder," U.S. Pat. No. 3,897,216 shows another apparatus in which cuvette trays are unloaded from a supply stack, synchronously advanced by a chain drive in front of a photo-optical reader, and then restacked into an output tray.

Some prior art units have also included photo-optical codings associated with each specimen read by the apparatus. For example, Carter et. al., "Automatic Clinical Analyzer," U.S. Pat. No. 3,770,382 shows a disposable test pack advanced on a belt through an automated apparatus which photo-optically reads the reaction in each sample chamber as well as an optically bar coded strip containing information which identifies the type of test for which the pack is designed.

However such prior art apparatus is of such a design and nature that the units are typically large and complex. Such automated apparatus for immunoassay enzyme testing is generally designed for use in specialized laboratories where the number of samples which may be tested are in the hundreds or thousands and where the operator of such equipment specializes generally in laboratory procedures and in particular in a high volume processing in an automated immunoassay testing apparatus. Therefore, the equipment is not only large and complex, but requires a high degree of operator skill or specialization, and a high volume usage in order to efficiently utilize the apparatus.

What is needed then is an enzyme immunoassay apparatus and methodology which can be reduced to practice in a small and economic unit which can be operated and run by an occasional and nonspecialized user. The design and methodology must further be of such a nature that it can be economically and efficiently utilized at small volumes with a plurality of tests.

BRIEF SUMMARY OF THE INVENTION

What is described here is an asynchronous serial cuvette reader or what is equivalently labeled as a chemistry analyzer scanner. Whereever referenced "asynchronous serial cuvette reader" shall mean the same invention as labeled by the terms "chemistry analyzer scanner". The invention is an apparatus for optically measuring the contents of a plurality of cells comprising a photoemitter for emitting light, and a photodetector for detecting light received from the plurality of cells upon exposure of the cells to light emitted from the photoemitter. A first circuit for detecting abrupt changes in light received by the photodetector is coupled to a second circuit for establishing a measurement of the light received by the photodetector after an abrupt change detected by the first circuit. By this combination of elements the plurality of cells is arbitrarily and asynchronously measured.

The first circuit for detecting abrupt changes in the light comprises a circuit for comparing the intensity of the light currently being received by the photodetector with the intensity of the light previously received by the photodetector.

The circuit for comparing the intensity of the light currently received and previously received compares the currently received intensity of light to a computed moving average of the intensity of the light previously recieved by the photodetector.

The circuit for detecting abrupt changes in the intensity of light received by the photodetector detects the abrupt changes from edges of each one of the plurality of cells.

The invention further comprises an assembly for holding the plurality of cells in a linear array, an open channel with the photoemitter being disposed on one side of the open channel. The assembly of cells is linearly arranged and is configured for manual displacement along the channel adjacent the photoemitter and photodetector. A third circuit modulates the light in a predetermined pattern. Thus the first circuit detects the light from the photoemitter only if modulated in the predetermined pattern, so that the open channel can be open to ambient light.

Alternatively the invention can be thought of as an apparatus for optically measuring a plurality of cells comprising a photoemitter for generating a sensing beam of light, a photodetector for detecting intensity of the beam of light, and a circuit for asynchronously reading the optical density of each of the plurality of cells as the cells are moved adjacent to the photoemitter and photodetector.

In particular the circuit for asynchronously measuring the optical density of each of the plurality of cells detects abrupt changes in optical density and interprets the abrupt change as a cell edge. Optical density measurements made between cell edges are established as an accepted measurement.

The circuit for asynchronously measuring the optical density compares currently measured optical densities with a computed moving average of previously measured optical densities.

The invention is also a method for optically measuring a plurality of cells comprising the steps of moving the plurality of cells adjacent to a photoemitter and photodetector at an arbitrary rate; measuring a plurality of values of light intensity other than ambient light received by the photodetector; detecting an abrupt change of the light intensity received by the photodetector; and storing a first measure of at least one of the plurality of values of the light intensity after detection of the abrupt change of the light intensity.

The step of detecting an abrupt change in intensity of the light comprises the steps of: storing a second measure of at least one of the plurality of values of the light intensity; and comparing at least one of the plurality of values subsequently produced by the step of measuring with the second measure. The method further comprises the step of selectively performing the step of storing the first measure of the plurality of values of the light intensity as an accepted measurement in response to the step of detecting an abrupt change.

The second measure of the plurality of values is a moving average of a predetermined number of values.

The step of detecting an abrupt change in the light intensity comprises the step of: detecting the edge of one of the cells; and thereafter selectively storing the second measure as an accepted measurement.

Finally the invention includes a method of asynchronously, optically measuring the contents of a plurality of sample cells comprising the steps of: manually moving the plurality of sample cells adjacent to a source of light and a detector of light; quantifying the light intensity received by the detector of light at predetermined time periods; detecting an abrupt change in the intensity of the light during one of the predetermined time periods; determining if the abrupt change in the intensity of the light persists for a predetermined number of the time periods; and storing a value corresponding to the intensity of the light quantified during one of the predetermined time periods contingent upon the step of determining establishing persistence of the abrupt change in the light intensity.

Turn now to the following figures wherein like elements are referenced by like numerals.

Figure 1:
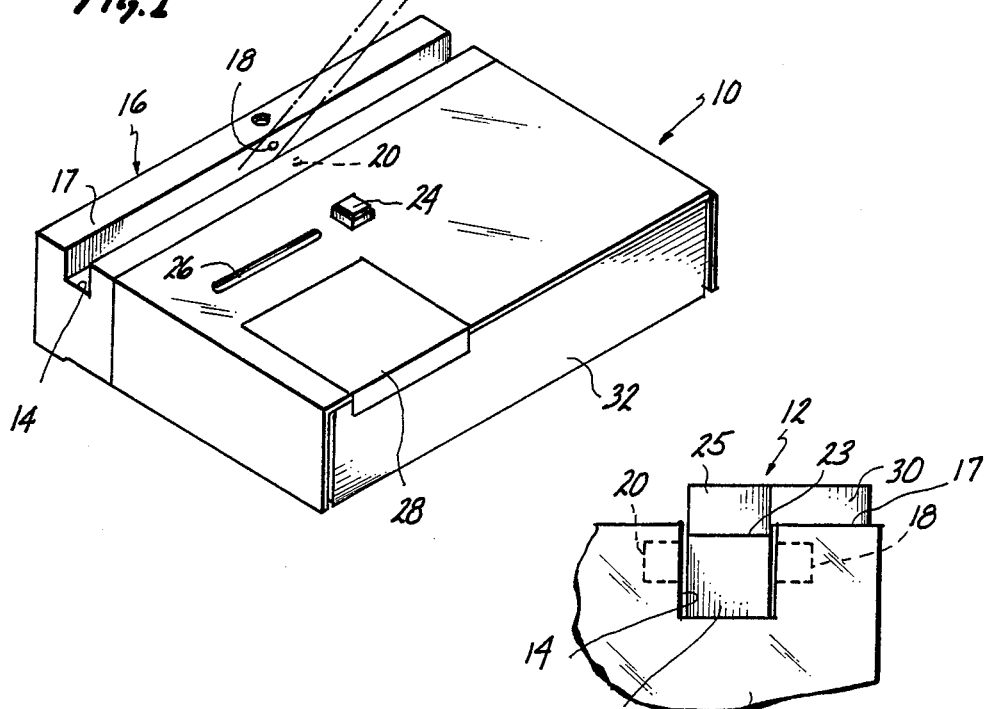
FIG. 1 is a rear perspective view of an enzyme immunoassay device incorporating the invention showing the insertion of an immunoassay cuvette in the open light slot of the apparatus.

The invention and its various embodiments may now be better understood by turning to the following detailed description of an illustrated embodiment.

DETAILED DESCRIPTION OF THE PREFERRED EMBODIMENTS

The present invention includes an apparatus and method for conducting enzyme immunoassay tests on a plurality of specimens wherein the specimens are contained within an assembly, such as a cuvette tray, and are asynchronously moved through a light detecting apparatus. In the preferred embodiment, movement of the cuvette tray is performed by manually translating the cuvette tray along an open channel defined in and along the front edge of the chassis of the apparatus. The light source and detector are on opposite sides of the cuvette and transmitted light is read. However, it is expressly within the scope of the invention that the light source and detector may be on the same side of the cuvette and that reflected, fluorescent, scattered and luminescent light may be detected or read. Furthermore the cuvette itself may or may not be provided with gaps between individual cells in the cuvette. It is further within the scope of the invention that the specimens may be contained in discrete tubes of cells which are not connected in a cuvette tray assembly. The invention still further provides a means for kinetic measurements of changes in the optical properties of the cells by repetitive reading of the cells in separate passes through the channel with effective elimination of delays between measurements during a given pass thereby obviating the stopping of the kinetic reaction. Arbitrary software instructions or identifications are also read from a bar code attached to the cuvette tray to instruct a resident central processing unit within the apparatus as to the nature of the sample, its order and the data reduction scheme to be performed.

For example, in the illustrated embodiment, the first character on the bar code strip is a start character signifying the beginning of the bar code information. The next codes indicate the number of tubes which are in the rack and whether the tubes are separated by gaps or not. A scale factor relating to the standard point values are then read. Thereafter, the number of standard points relating to the particular test are specified and the data reduction to be performed to establish the standard curve between the standard points is defined. The values for the standard points are next serially read. Next follows characters which represent the name of the test, usually four alphanumeric characters or less. The dimensional units of the test parameter are then given, followed by an optional data space. In this optional space, such information as expiration date of the test cuvette, serial number of the cuvette, or other user information or messages can be included. The bar code then ends with a checksum used in an error checking routine to detect two or other multiple bit errors, and finally a stop code. Clearly, this format can be changed to many other forms and still be included within the teaching of the invention. The preferred code has been set forth only to give an example of the type of operations which are performed in the illustrated embodiment.

Typically, a number of the order of ten samples or specimen cells is contained within a cuvette tray which is approximately four to five inches in length. The ten cells are thus manually translated in front of the photodetector disposed in a light channel and read within the time period of one or two tenths of a second or less. This provides a near simultaneous reading of the multiple specimens in the cuvette by an apparatus which has no electromechanical moving parts, which is small and compact, and which can be economically manufactured and used by a relatively unskilled operator. The invention and its various embodiments can be better understood by now specifically turning to the perspective views of FIGS. 1 and 2.

Figure 3:
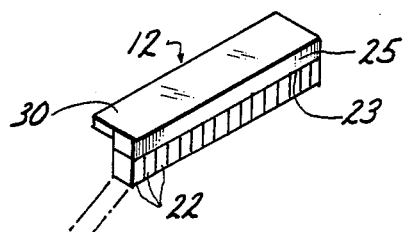
FIG. 3 is a fragmentary end elevational view in enlarged scale of the end or side of the apparatus shown in FIG. 2.
Figure 2:
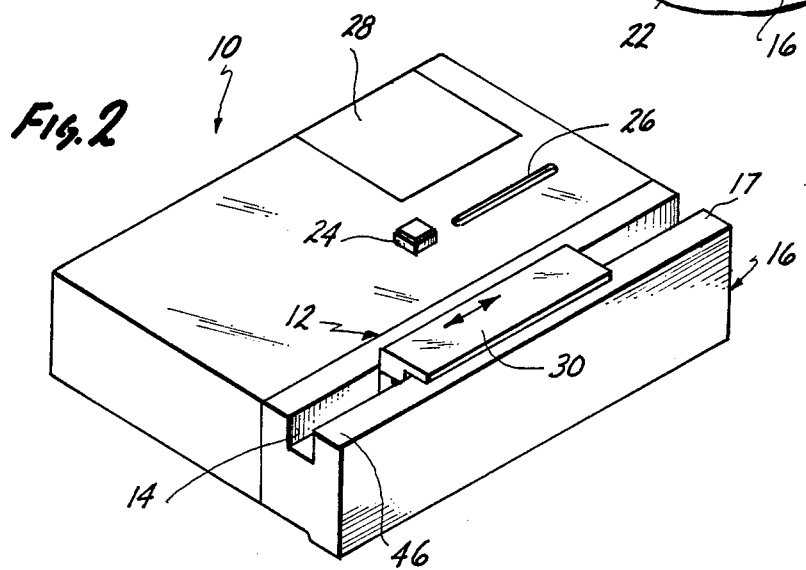
FIG. 2 is a front perspective view of the apparatus of FIG. 1 shown with a cuvette tray in place.

FIG. 1 shows a rear perspective view of a chassis, generally denoted by reference numeral 10, into which a cuvette tray, generally denoted by reference numeral 12, is inserted. FIG. 2 is a front perspective view of chassis 10 wherein tray 12 has been inserted and moved midway through channel 14 defined in the front edge of chassis 10. Channel 14, as shown in the perspective drawings of FIGS. 1 and 2 and better shown in the enlarged partial side elevational view of FIG. 3, is a straight open channel defined in a solid facing block 16 of chassis 10. Block 16 has disposed therein a photoemitter, generally denoted by reference numeral 18 and a photodetector, generally denoted by reference numeral 20. A beam of light of a predetermined frequency spectrum is transmitted from photoemitter 18 across channel 14 to opposing photodetector 20. Sample tray 12 is manually disposed in and translated through channel 14 such that each cell 22 within tray 12 will be disposed between photoemitter 18 and photodetector 20 in the beam of radiation or light therebetween. As will be described in greater detail below, a plurality of sample cells 22 are included within tray 12 and are translated through the sensing light beam at an arbitrary speed and timing. The circuitry, described in greater detail in connection with FIGS. 4–6, detects the edge of each sample cell 22, compensates for any surface irregularities or blemishes on each cell 22, and reads the photo-optical density or translucence of the material contained within cell 22.

Referring particularly again to FIGS. 1 and 2, it can readily be noted that according to the invention an arbitrary number of specimens or sample cells 22 are simply manually laid within channel 14 and quickly translated through the sensing beam between photoemitter 18 and photodetector 20. The linear speed in channel 14 of tray 12 may thus be arbitrarily set during any single traversal of the sensing light beam and will arbitrarily vary between separate traversals of the same sample tray 12 or of additional sample trays 12. No moving electromechanical parts are required to read the specimens nor is there any complex or expensive synchronization circuitry or methodology to be observed or controlled.

In the illustrated embodiment, chassis 10 includes a conventional paper strip printer (not shown) for which a single control button 24 is shown which is a paper advance control, a paper output feed slot 26 and a paper feed door 28 to allow the user to access the paper feed of the printer included within chassis 10.

Although not shown particularly in the drawings, tray 12 may also include a printed or paper strip bearing an optically readable bar code. Such a strip may for example be placed upon one edge of cells 22 and simultaneously read with cells 22, or preferably placed along an opposing tab 30 of tray 12 or on the under side of tray 12, as best shown end view in FIG. 3. Tray 12 would thus be first inserted such that depending side 30 of tray 12 was first disposed into channel 14 and underside 15 disposed flushly against edge 17. The tray is then manually advanced between photoemitter 18 and photodetector 20. While photoemitter 18 and photodetector 20 reads cells 22 in tray 12, a conventional optical bar code reader (not shown in FIGS. 1–3, but described in the schematics of FIGS. 4 and 5) disposed into surface 17 or the front side of block 16 as appropriate reads the corresponding bar code. The bar code is then read to provide the enclosed circuitry with information as to the nature and number of the samples, the test to be run and the data report required. When cells 22 are translated through the sensing light beam, the optical density of each of the cells is read in a manner more particularly described below. The photo-optically read data is then processed according to the instructions contained on and taken from the previously read bar code strip.

Alternatively, tray 12 could be accompanied by a removable bar code strip, such as might be adhesively retained on tray 12. In such an embodiment emitter 18 and detector 20 could double to read both the bar code and the optical densities of cells 22. The strip would then be removed from the tray, separately disposed into channel 14 and translated through the sensing light beam. This alternative embodiment is mentioned to illustrate the scope of the invention. In the illustrated embodiment depicted in the Figures, a separate bar code reader is provided and the optical densities of cells 22 and the bar code are simultaneously read by separate reading means.

The nature of information in the bar code is arbitrary, and it must be clearly understood that it is within the scope of the invention that generalized instructions may be included in the bar code which will configure the processing unit contained within chassis 10, as described in greater detail in connection with FIGS. 4–6, to implement an arbitrarily defined test protocol. The illustrated test sequence described below is not limited to the performance of any given number of enzyme immunoassay tests, any class of such tests or, even enzyme immunoassay tests, but could be generally instructed by the optical bar code input to arbitrarily perform any data input, analysis or reporting function. Therefore, the report printed on the paper strip output (not shown) through slot 26 could be easily changed from time to time to provide any number of report formats even with a single enzyme immunoassay test. Such a bar code instruction would thus also be capable, at least to an extent, to allow the user to select from one among a plurality of test protocols or report formats.

Although not specifically shown in the depiction of FIG. 1 and even though the illustrated embodiment describes the output format simply through a single paper strip medium, it is expressly included within the invention that any number of additional output ports may be included and typically installed along back panel 32 of chassis 10 as shown in FIG. 1 to allow coupling to conventional computer-driven printers, modems, or other computer units and peripherals.

Figure 4:
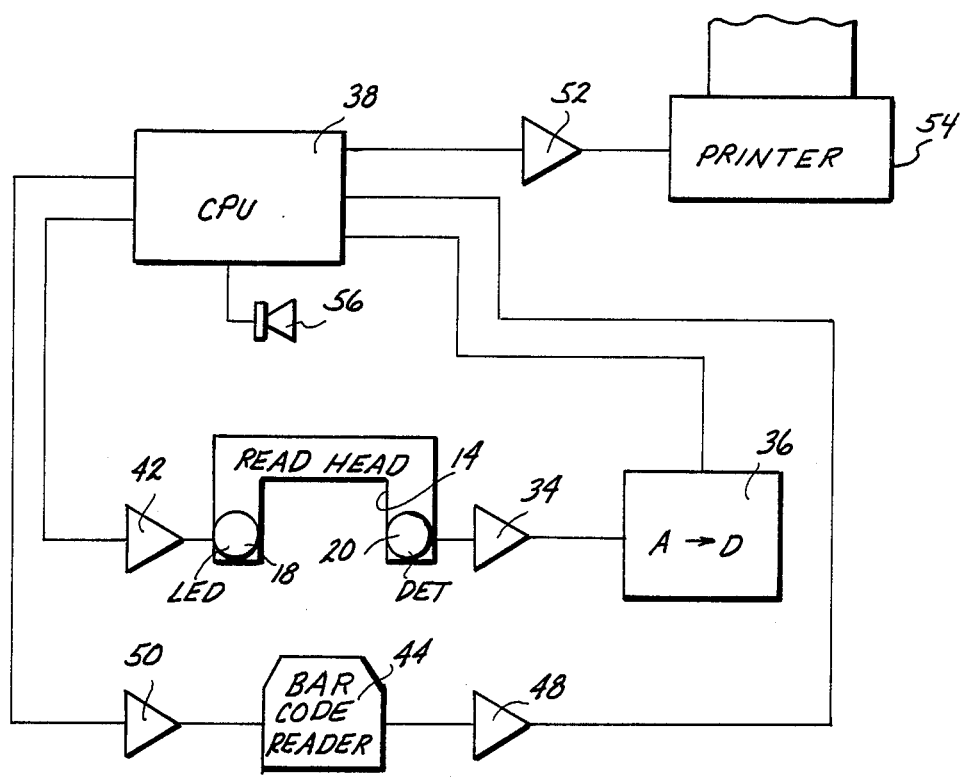
FIG. 4 is a simplified block diagram of the apparatus incorporating the invention.

Turn now to FIG. 4 wherein a block diagram of the apparatus is depicted. The photo-optical read head is comprised of channel 14 defined in block 16 of chassis 10. As previously described, a light emitting diode 18 or, other modulated or unmodulated light source, generates a light beam which is transmitted across channel 14 and received by photo-detector 20. The output of detector 20 is conditioned or amplified by amplifier 34 and then converted into digital format by a fast analog-to-digital converter 36. The output of converter 36 is then provided to a conventional central processing unit (CPU) 38. CPU 38 is coupled to an amplifier and conditioning circuit 42 whose output in turn is coupled to light emitting diode 18. Thus CPU 38 is able to control and modulate the output of diode 18 to implement the detection protocol.

Similarly, a separate conventional bar code reader 44 may be disposed in channel 14, such as within the base of channel 14 or within upper edge 46 of block 16 to read a coded strip attached to specimen tray 12. The output of bar code reader 44 is similarly amplified and conditioned by amplifier 48 and provided as an input to CPU 38. The photoemitting unit within conventional bar code reader 44 can be similarly powered or controlled by CPU 38 acting through amplifying and conditioning circuit 50 coupled therebetween. The output of CPU 38 is buffered through amplifier 52 to a conventional paper strip printer 54. Similarly, an output of CPU 38 as coupled to an audio output unit 56 such as a speaker or a triggerable audio generator for generating an audible feedback signal to the user to indicate: that the sensing beam between light emitting diode 18 and detector 20 has been interrupted; and that a successful or unsuccessful test and analysis has been completed.

Figure 5:
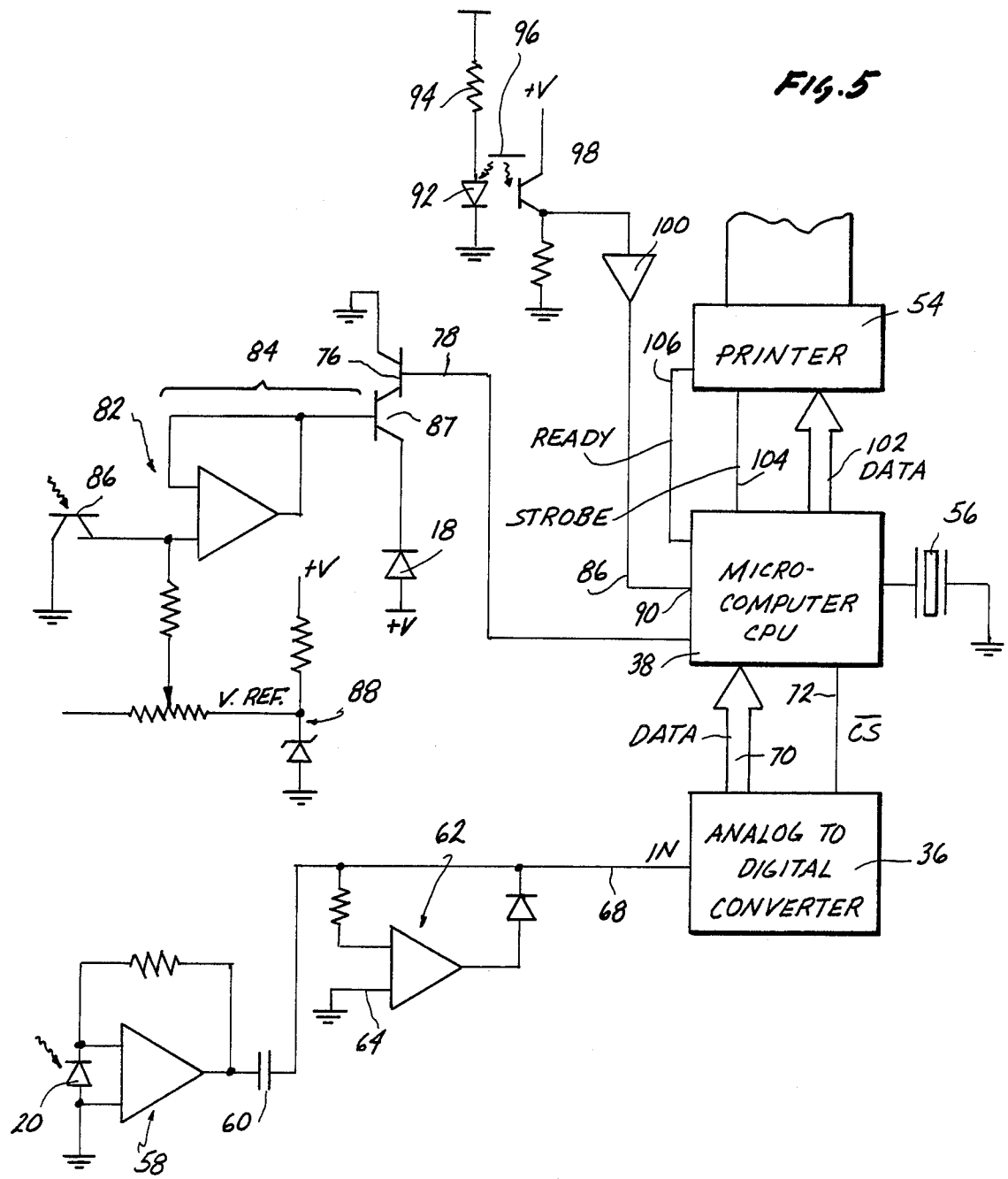
FIG. 5 is a more detailed schematic diagram of operative portions of the circuitry outlined in FIG. 4.

Turn now to the somewhat more detailed schematic of the circuitry shown in FIG. 5 wherein like elements have been referenced by like numerals. Begin again by considering photodetector 20. The output of detector 20 is coupled to a buffer amplifier generally denoted by reference numeral 58. The output of transconductance amplifier 58 is capacitively coupled through capacitor 60 to the input of a a voltage clamp and gain stage amplifier, generally denoted by reference numeral 62. It is contemplated that the specific circuit configurations used to buffer and amplify the output of photodetector 20 to a signal level and impedance compatible with an input 68 of analog-to-digital converter 36 could assume any design now known or later devised in the art.

The output of voltage clamp and gain stage amplifier 62 is provided through input 68 to A-to-D converter 36. A parallel data output is provided on bus 70 to the data input of microprocessor 38. Microprocessor 38 is a conventional microprocessor as described before, and in the illustrated embodiment is model number MC 68705P3 manufactured by Motorola Semiconductor of Austin, TX. CPU 38 is coupled to a conventional conversion start line 72 of A-to-D convertor 36.

Consider now the circuitry connected with the light emitting diode 18. Diode 18, coupled between, ground and the voltage supply, is modulated through device 76 whose gate is resistively coupled to an output line 78 of CPU 38. Therefore, LED 18 is modulated according to control provided by CPU 38. In the illustrated embodiment the spectrum of diode 18, which is in the red region, is modulated by CPU 38 by a 3 kilohertz square wave. The chopped or modulated light beam is received by photo-detector 20 and converted into a similarly modulated received signal which is ultimately converted to digital format and coupled back to CPU 38 on data bus 70. Modulating or chopping of the light beam under CPU control allows the sensing beam to be transmitted across channel 14 in open or ambient light without any difficulty. Any interference or noise caused by ambient light are thus invisible to CPU 38 which sees and only looks for a modulated 3 kilohertz signal. The modulation of the optical sensing signal thus allows sample tray 12 to be manually inserted and manually drawn through the sensing beam through the open channel 14 in a very simple and economical optical arrangement.

Light emitting diode (LED) 18 is further modulated by means of device which is coupled in series between device 76 and LED 18. The gate of control device 80 in turn is coupled to a beam stabilization circuit, generally denoted by reference numeral 82. Beam stabilization circuit 82 is comprised of an amplifier, generally denoted by reference numeral 84, and a beam monitoring phototransistor 86 coupled to the input of amplifier 84. Phototransistor 86 is preferably although not necessarily physically disposed next to LED 18 so that it is irradiated by the sensing light beam from LED 18. The bias of amplifier 84 is adjusted by means of variable resistor 88 according to conventional design. The variable tap on resistor 88 is coupled with the output of phototransistor 86 to the input of amplifier 84 and therefore ultimately allows manual and automatic adjustment of the driving signal to LED 18. However, in the event that the characteristics of LED 18 varies and its output begins to change, these changes will be detected by phototransistor 86. The bias of amplifier 84 is changed so that a change of the light energy received by phototransistor 86 will ultimately serve to inversely change the driving voltage applied to LED 18 thereby keeping the output of LED 18 substantially constant or at least above a minimum threshold value. LED 18 is modulated by CPU 38 to provide a modulated driving voltage to LED 18 through controlling transistor 87 whose gate is coupled to the output of amplifier 84.

Now having considered the circuitry corresponding to the sensing beam, turn to another one of the input circuits coupled to CPU 38. A conventional bar code reader 44 is shown as having its output coupled to an input terminal 86 of CPU 38. In the illustrated embodiment a red light emitting diode 92 is coupled between the power supply through a limiting resistor 94 and ground. Light from diode 92 is transmitted to paper tape 96 containing the optical bar code. Reflected light is then received by phototransistor 98 which is modulated according to the bar code drawn across the light beam from diode 92. The output of phototransistor 98 is in turn coupled to the input of transconductance amplifier 100. A series of asynchronous pulses is then generated at the output of trigger 100 according to the bar code which is read and coupled to input 90 of CPU 38. Asynchronous serial data is then read by CPU 38 and processed according to conventional means. As previously stated and as can now be readily appreciated the bar code may embody not only patient identification, the number of sample cells, the test to be run, but also an arbitrary format instruction. A general processing program may be further be included within the resident erasable programmable read only memory (EPROM) included within CPU 38 (not separately shown). This general program may then receive arbitrary software instructions through the bar code reader 44 through the circuitry just described to process data received from data bus 70 and to report the data as described below.

In the illustrated embodiment and as discussed previously in connection with FIG. 4, a conventional paper tape printer 54 is coupled to the output data bus 102 linking CPU 38 and printer 54. In addition one or more discrete control signals are coupled therebetween such as a strobe signal on line 104 and a ready signal on line 106 coupled between printer 54 and CPU 38. The strobe and ready signals are conventional and are used to synchronize the printer to the data output on bus 102, and to provide a hand shake between printer 54 and CPU 32 to indicate the availability of printer 54 to receive data.

As further previously described printer 54 need not be the only output device included within the apparatus. In fact, in the illustrated embodiment a piezoceramic audio generator or beeper 56 is also coupled to one of the output lines of CPU 38. Beeper 56 is selectively activated to provide an immediate audio feedback to the operator to communicate readiness to accept data, to transmit data and to indicate the successful or unsuccessful analysis thereof or any other user prompt. It is expressly contemplated, for example, that CPU 38 is capable of driving beeper 56 with a plurality of distinguishable audio signals each of which may have a different significance.

Furthermore, although not shown in the illustrated embodiment of FIG. 5, it is entirely within the scope of the invention that additional output ports from CPU 32 can be appropriately coupled to output data bus 102 according to conventional design principles to allow connection to modems, disk drives, XY plotters, or other computers and their peripherals.

Figure 6:
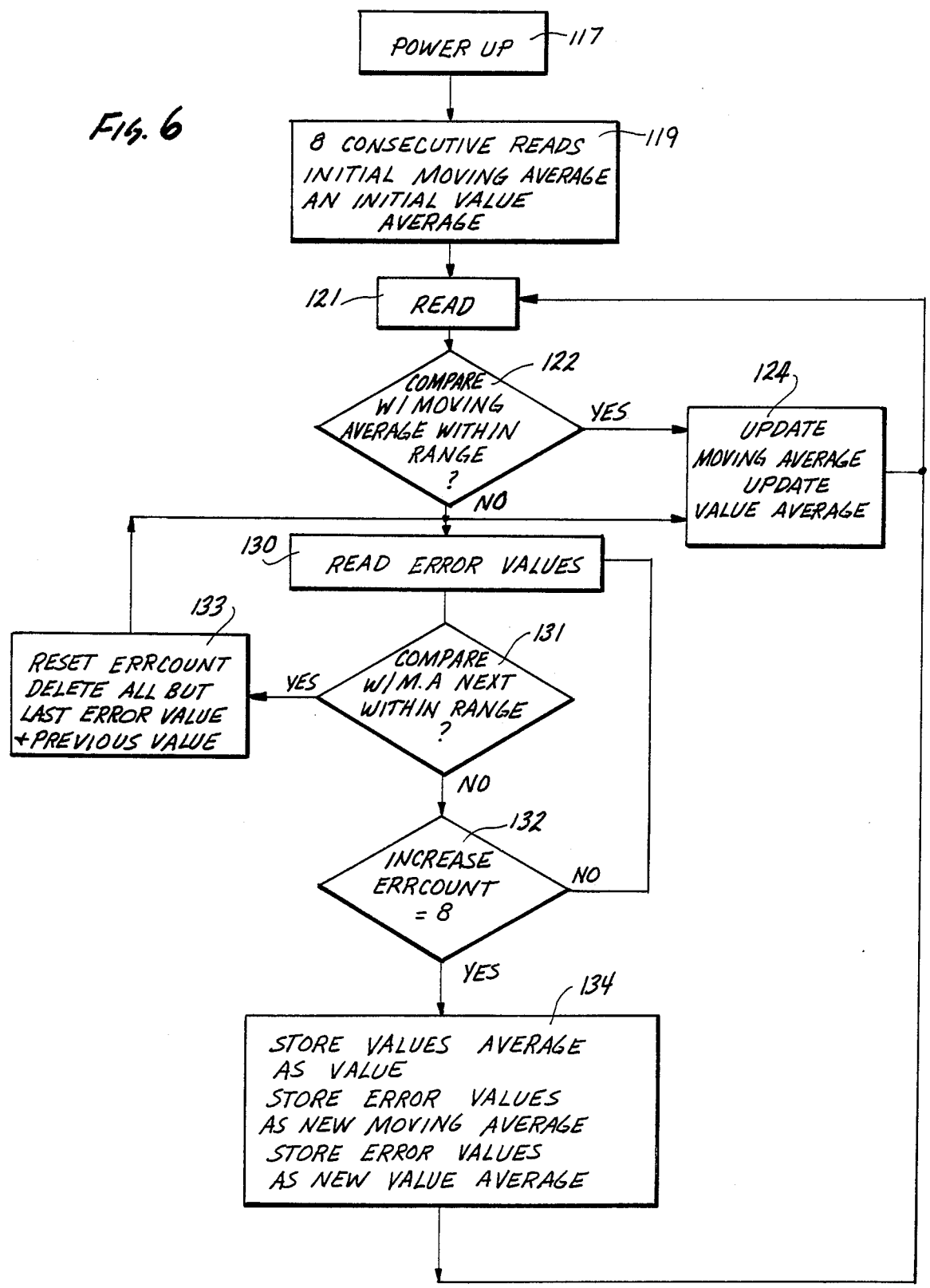
FIG. 6 is a flow diagram of the methodology of the invention.

Turn now to FIG. 6 and consider an outline of the method of the invention as implemented by the circuitry of FIGS. 4 and 5 and as diagrammatically summarized in the flow diagram of FIG. 6. Firstly, tray 12 is placed within channel 14. CPU 38 has been powered up together with the sensing circuit corresponding to LED 18 and photodetector 20 and bar code reader 44. After power up, the value of the light intensity of the sensing beam as read at step 108. The time required to read a value is determined by A-to-D converter 36 and data analysis which is normally approximately 200 microseconds. The value read by A-to-D converter 36 is thus loaded during the read cycle into an appropriate register within CPU 38 under software control.

Before considering the actual implementation of the flow diagram of FIG. 6, first consider the establishment of acceptable measurements of the samples generally. The sample cells represent a series of optical domains, a domain corresponding to the space between cells, a domain corresponding to the space between the leading and trailing edges of each cell wall, and a domain corresponding to the contained sample itself.

A moving average is initially established from eight consecutive read operations. After following the establishment of the initial moving average, the moving average is updated by decreasing the weight of the prior moving average by one read value as each new read operation is completed and the new read value is averaged into the thusly weighted old average to form the new moving average. The cumulative average of a domain is stored as the value average in CPU 38.

The read operation is comprised of of a read phase and an interphase. During the read phase the sample light level and bar code light level are sensed to determine if there has been a change. During the interphase of the read operation the bar code characters are decoded, but generally remain uninterrupted. Once the first fields of the bar code is read, it is then checked in CPU 38 to determine the number of sample cells which exist, and the number of walls separating the cells, since in some cuvettes shared walls may exist.

The read value of the light intensity is compared at each sample point to the moving average. If the compare indicates an abrupt change as defined by a change beyond a predetermined ratio or range, the read and compare steps are repeated a number of times, such as eight or more times, to verify the validity of the optical change. Upon confirmation of a real optical change, the value average is stored in CPU 38 as the accepted measured value of prior domain and a new moving average and new value average is established as as the next domain is traversed. The read operation continues until the number of accepted measurements equals the number of different optical domains that exist as defined by the previously or simultaneously read bar code.

Initially a moving average of eight values are read to define a short term moving average. Further read values are then compared against the short term moving average to determine if an abrupt change has occurred as would be expected when an optical domain is traversed. This allows a slowly changing value to be read without being treated as an abrupt change characteristic of the transversal of an optical domain. Such slowly varying values would occur in the sampling of round or cylindrical sample cells where the diametric sample length changes as the cell moves through the beam.

Turn now to the specific illustration of FIG. 6. After power up at step 117 and intitialization at step 119, a value is optically read at step 121. If the read value is within a predetermined range of the moving average of the last eight values as determined at step 122, then the moving average and a cumulative value average is updated at step 124 by averaging in the last read value with the previous seven values to obtain a new eight-value moving average. The moving average is initially considered as the first eight read values after power-up. The process then returns to step 121 for the next read or sampled value.

If the read value at step 122 in FIG. 6 is out of the predetermined range, e.g. more than 20 percent different than the moving average, then a first error value is read at step 130 and compared to old moving average at step 131. If this first error value is in range then the out of range value is treated as an erroneous reading or non-data noise. The error count is reset and all but the last error value is ignored at step 133. Thereafter, processing returns to step 124 where new moving and value averages are established. If this error value is out of range eight consecutive times as determined at step 132, the moving and value average is then replaced by the error average computed from the eight consecutive out-of-range error readings and the previous value average is stored as the accepted measured value at step 134. The accepted measurement is stored within the resident memory within CPU 38. The next value is then read at step 121. A determination is made at step 121 whether or not the measurement just made is the last measurement required or whether there is an expectation of additional measurements according to the instructions read from the bar code reader. If the last measurement has been made, then the program exits at step 121 from the measurement phase and will enter a processing and output phase as appropriate. Each of these phases may be arbitrarily controlled according to software instructions, again read from the bar code reader, and are therefore not detailed to any extent in the illustrated embodiment. If the last measurement has not been made, then a new value is read.

Alternatively, the moving average could be first established with a small number of read operations, e.g. eight, and then an average continued to be created on the next 1000 read operations or until a domain boundary is encountered. Thereafter, the moving average could then be maintained based on 1000 readings to provide a protocol less sensitive to short term changes in optical density.

By incorporating a fast sampling rate within A-to-D converter 36 and by determining the existence of an acceptable measurement by comparison with the moving average, abrupt changes in light level intensity are selectively identified. Therefore before cuvette tray 12 is displaced within the sensing beam, a first predetermined moving average will be established which is indicative of simple transmission across channel 14. Thereafter, the first sample cell 22 of cuvette tray 12 is moved into the beam causing an abrupt change in the light intensity. As the beam moves through the edge of the sample cell the currently read value of the transmitted beam will vary dramatically from the moving average established for the beam during the preceding time period and during the initial time period during which the edge of the sample cell 22 breaks the beam. However, as sample cell 22 continues to move through the beam the moving average will be readjusted to be indicative of the optical density of the material within the sample cell, including such effect as the walls of the sample cell themselves may have. At least by the time the midpoint within sample cell 22 is reached the moving average will be established and an acceptable measurement generated. A measured value is thus established for each domain.

As sample cell 22 continues through the beam a second abrupt change in light intensity occurs as the beam begins to penetrate the following side wall and move out of sample cell 22. Again the currently read value will vary drammatically from the moving average established in sample cell 22. The process then will continue with each of the remaining cells in cuvette tray 12. What results is a series of stored measurements within the resident memory of CPU 38 indicative of measurements within the sample cell and at points between (and outside where a gap exists between each sample cell) each sample cell 22.

One or more cells within cuvette tray will be control cells to allow the processing system to subtract out any effect of the optical qualities of cuvette tray 12 thereby leaving a computed measurement indicative of the enzyme immunoassay reaction within each test cell. This measurement is then subject to further processing under software control to establish concentrations or activity of the analyte according to the specific reagent used in each cell. Again, the number of cells, the reagents in each cell, the identification of which cells are control cells, whether there a any open gaps between cells, and the like can be read from the optical bar code strip together with needed computational constants or data drawn as appropriate from resident memory. Thereafter once the percentages of the desired enzymes have been determined, a report can be printed by printer 54 or otherwise displayed.

Several points should be noted with respect to the process as described above. Firstly, no particular synchronization is required as was typical in the prior art to read each of sample cells 22. The circuitry itself detects and identifies the edges of each sample cell 22 and cuvette tray 12 and in response thereto appropriately fixes a measurement of the test within each cell. This lack of any need for synchronization allows cuvette tray 12 to be read at an arbitrary and varying rate and thus allows the cuvette tray to be hand fed through the sensing beam. Minor imperfections in the measured optical path are filtered out by use of the moving average as well. For example, any scratches or other minor optical imperfections within the walls of sample cells 22 of cuvette tray 12 are averaged out.

In any case, sample cells 22 are asynchronously read without any particular restriction made with respect to timing or uniformity of speed. If for any reason the user translates cuvette tray 12 through the sensing beam at a speed which is too slow or too fast to establish a reliable or acceptable series of measurements, CPU 38 simply informs the user through beeper 56 of the unsuitability by an appropriate audio signal and the user can conform his manual manipulation of cuvette tray 12 until a speed fast enough or slow enough has been achieved to allow proper operation of the circuitry. While as a practical matter cuvette tray 12 may not be moved through the light beam at either an infinitely slow or fast rate, the range of rates which are acceptable is wide, typically ranging from 0.1 centimeters per second to 25.4 centimeters per second. It has been found that the user has no difficulty quickly learning to move cuvette tray 12 through the sensing beam at a speed within this range.

Many alterations and modifications may be made by those having ordinary skill in the art without departing from the spirit and the scope of the invention. The illustrated embodiment has been described only to serve as an example and it should not be read as limiting the invention which is defined in the following claims.

I claim:

1. A method of asynchronously, optically measuring the contents of a plurality of sample cells without any timing indicia comprising the steps of:

manually moving said plurality of sample cells adjacent to a source of light and a detector of light;

quantifying the light intensity received by said detector of light at predetermined time periods:

detecting an abrupt change in said intensity of said light during one of said predetermined time periods:

determining if said abrupt change in said intensity of said light persists for a predetermined number of said time periods: and storing a value corresponding to said intensity of said light quantified during one of said predetermined time periods when said step of determining establishes persistence of said abrupt change in said light intensity where said step of detecting said abrupt change in said intensity of said light comprises the steps of:

computing a moving average of quantified values of said light intensity as quantified during a predetermined proceeding number of said time periods;

where said step of determining includes the step of comparing a quantified value of said intensity of light to the just previously computed moving average; and where said step of storing said value corresponding to said intensity of said light is performed only if said step of comparing indicates a difference between said quantified intensity of said light over said moving average by a predetermined amount.

* * * * *